US011219677B2

(12) United States Patent
Chang et al.

(10) Patent No.: US 11,219,677 B2
(45) Date of Patent: Jan. 11, 2022

(54) IMMUNOTHERAPY OF CANINE LEISHMANIASIS

(71) Applicant: Rosalind Franklin Univ. of Medicine and Science, North Chicago, IL (US)

(72) Inventors: Kwang-Poo Chang, Kenilworth, IL (US); Laura Manna, Naples (IT); Raffaele Corso, Naples (IT); Bala K. Kolli, North Chicago, IL (US)

(73) Assignee: Rosalind Franklin University of Medicine and Science

( * ) Notice: Subject to any disclaimer, the term of this patent is extended or adjusted under 35 U.S.C. 154(b) by 0 days.

(21) Appl. No.: 15/970,540

(22) Filed: May 3, 2018

(65) Prior Publication Data

US 2018/0318408 A1 Nov. 8, 2018

Related U.S. Application Data

(60) Provisional application No. 62/502,214, filed on May 5, 2017.

(51) Int. Cl.
*A61K 39/008* (2006.01)
*A61K 41/00* (2020.01)
*A61K 41/17* (2020.01)
*A61K 39/00* (2006.01)

(52) U.S. Cl.
CPC ........ *A61K 39/008* (2013.01); *A61K 41/0057* (2013.01); *A61K 41/17* (2020.01); *A61K 2039/521* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 6,890,542 B2 * | 5/2005 | Mottram | A61K 39/008 424/269.1 |
| 6,897,542 B2 | 5/2005 | Mottram et al. | |
| 7,238,347 B2 | 7/2007 | Chang et al. | |
| 7,261,887 B2 | 8/2007 | Chang et al. | |
| 9,327,017 B2 | 5/2016 | Chang et al. | |
| 2012/0288524 A1 * | 11/2012 | Chang | A61K 39/008 424/269.1 |
| 2017/0042989 A1 | 2/2017 | Chang et al. | |

FOREIGN PATENT DOCUMENTS

WO 2006105044 A1 10/2006

OTHER PUBLICATIONS

Manna et al. Parasites and Vectors (2015) 8:289 p. 1-9.*
Chang et al. Parasites and Vectors (2016) 9:396 pp. 1-13.*

Gramiccia, M. et al. "HIV-Leishmania co-infections in Italy, Isoenzyme characterization of Leishmania causing visceral leishmaniasis in HIV patients"; Trans. of The Royal Society of Tropical Medicine and Hygiene; 1992; 86:161-163.
Gumy, Alain et al. "The murine model of infection with Leishmania major and its importance for the deciphering of mechanisms underlying differences in Th cell differentiation in mice from different genetic backgrounds"; Int. J. for Parasitology; 2004; 34:433-444.
Harth, Yoram et al. "Modified Topical Photodynamic Therapy of Superficial Skin Tumors, Utilizing Aminolevulinic Acid, Penetration Enhancers, Red Light, and Hypothermia"; Dermatology; 1998; 24:723-726.
Hodgkinson, V.H. et al. "Leishmania amazonensis: Cultivation and Characterization of Axenic Amastigote-like Organisms"; Experimental Parasitology; 1996; 83:94-105.
Houde, Mathieu et al. "Phagosomes are competent organelles for antigen cross-presentation"; Nature; Sep. 2003; 425:402-406.
Ilg, Thomas et al. "Phosphogycan Repeat-deficient leishmania mexicana parasites Remain Infectious to Macrophages and Mice" J. of Biological Chemistry; Feb. 16, 2001; 276(7):4988-4997.
Joshi, Phalgun B. et al. "The gene encoding streptothricin acetyltransferase (sat) as a selectable marker for Leishmania expression vectors"; Gene; 1995; 156:145-149.
Kamhawi; Shaden et al. "Protection Against Cutaneous Leishmaniasis Resulting from Bites of Uninfected Sand Flies"; Science; Nov. 17, 2000; 290:1351-1354.
Kappas, Attallah et al. The Occurrence of Substances in Human Plasma Capable of Inducing The Enzyme s-Aminolevulinate Synthetase in Liver Cells: Medical Sciences; 1969; 64:557-564.
Lane, Nick "New Light on Medicine" Scientific American; Jan. 2003; 38-45.
Liu, Xuan et al. "The 63-Kilobase Circular Amplicon of Tunicamycin-Resistanct Leishmania amazonensis Contains a Funtional N-Acetylglucosamine-1-Phosphate Transferase Gene That Can Be Used as a Dominant Selectable Marker in Transfection"; Molecular and Cellular Biology; Sep. 1992; 12(9):4112-4127.
Lipoldova, Marie et al. "Mouse genetic model for clinical and immunological heterogeneity of leishmaniasis" Immunogenetics; 2002; 54:174-183.
Locksley, R.M. "Murine Cutaneous Leishmaniasis: Susceptibility Correlates with Differential Expansion of Helper T-Cell Subsets"; Annales de l'Institut Pasteur/Immunologie; 1987; 138(5):744-749; Elsevier Masson.
Melby, Peter C. et al. "The Hamster as a Model for Human Visceral Leishmaniasis: Progressive Disease and Imparied Generation of Nitric Oxide in the Face of a Prominent Th1-Like Cytokine Response" The J. of Immunology; 2001; 166(3):1912-1920.
Morris, Robin V. et al. "Sandfly Maxadilan Exacerbates Infection with Leishmania major and Vaccinating Against It Protects Against L. major Infection"; The J. of Immunology; 2001; 167(9):5226-5230.
Nadim, A., E. Javadian, and M. Mohebali. "The experience of leishmanization in the Islamic Republic of Iran." EMHJ—Eastern Mediterranean Health Journal, 3 (2), 284-289, 1997.
Olobo, Joseph O., Michael M. Gicheru, and Chris O. Anjili. "The African Green Monkey model for cutaneous and visceral leishmaniasis." Trends in parasitology 17.12 (2001): 588-592.
Pacheco, Raquel S., et al. "Chagas' disease and HIV co-infection: genotypic characterization of the Trypanosoma cruzi strain." Memórias do Instituto Oswaldo Cruz 93.2 (1998): 165-169.

(Continued)

*Primary Examiner* — Oluwatosin A Ogunbiyi
(74) *Attorney, Agent, or Firm* — Greensfelder, Hemker & Gale PC; Jared S. Manse

(57) ABSTRACT

The present invention provides a method for treating canine leishmaniasis by immunotherapy.

8 Claims, No Drawings

(56) References Cited

OTHER PUBLICATIONS

Probst, R. J., et al. "Rhesus monkey model for Leishmania major transmitted by Phlebotomus papatasi sandfly bites." Medical and veterinary entomology 15.1 (2001): 12-21.
Reed, Steven G. "Leishmaniasis vaccination: targeting the source of infection." The Journal of experimental medicine 194.3 (2001): F7-F10.
Requena, Jose M., et al. "Immune and clinical parameters associated with Leishmania infantum infection in the golden hamster model." Veterinary immunology and immunopathology 76.3-4 (2000): 269-281.
Sassa, S. "Delta-aminolevulinic acid dehydratase assay." Enzyme 28 (1982): 133-145.
Sassa, S., et al. "A microassay for uroporphyrinogen I synthase, one of three abnormal enzyme activities in acute intermittent porphyria, and its application to the study of the genetics of this disease." Proceedings of the National Academy of Sciences 71.3 (1974): 732-736.
Scott, Phillip, et al. "Immunoregulation of cutaneous leishmaniasis. T cell lines that transfer protective immunity or exacerbation belong to different T helper subsets and respond to distinct parasite antigens." The Journal of experimental medicine 168.5 (1988): 1675-1684.
Shaw, Jeffrey J. "Taxonomy of the genus *Leishmania*: present and future trends and their implications." Memórias do Instituto Oswaldo Cruz 89.3 (1994): 471-478.
Somanna, Ashwini, Vasanthakrishna Mundodi, and Lashitew Gedamu. "Functional Analysis of Cathepsin B-like Cysteine Proteases fromLeishmania donovani Complex Evidence for the Activation of Latent Transforming Growth Factor β." Journal of Biological Chemistry 277.28 (2002): 25305-25312.
Späth, Gerald F., et al. "The role (s) of lipophosphoglycan (LPG) in the establishment of Leishmania major infections in mammalian hosts." Proceedings of the National Academy of Sciences 100.16 (2003): 9536-9541.
Späth, Gerald F., et al. "Persistence without pathology in phosphoglycan-deficient Leishmania major." Science 301.5637 (2003): 1241-1243.
Späth, Gerald F., et al. "Identification of a compensatory mutant (lpg2-Rev) of Leishmania major able to survive as amastigotes within macrophages without LPG2-dependent glycoconjugates and its significance to virulence and immunization strategies." Infection and immunity 72.6 (2004): 3622-3627.
Tamar, Samira, Carole Dumas, and Barbara Papadopoulou. "Chromosome structure and sequence organization between pathogenic and non-pathogenic *Leishmania* spp." Molecular and biochemical parasitology 111.2 (2000): 401-414.
Valenzuela, Jesus G., et al. "Toward a defined anti-Leishmania vaccine targeting vector antigens: characterization of a protective salivary protein." The Journal of experimental medicine 194.3 (2001): 331-342.
Zhang, Kai, et al. "Sphingolipids are essential for differentiation but not growth in Leishmania." The EMBO journal 22.22 (2003): 6016-6026.
Chang, Kwang Poo et al. "Progress toward development of photodynamic vaccination against infections/malignant diseases and photodynamic mosquitocides" Proc. of SPIE vol. 10479 (2018); 1047912-1-1047912-15.
Dutta, Sujoy, Kayoko Waki, and Kwang Poo Chang. "Combinational sensitization of Leishmania with uroporphyrin and aluminum phthalocyanine synergistically enhances their photodynamic inactivation in vitro and in vivo." Photochemistry and photobiology 88.3 (2012): 620-625.
Dutta, Sujoy, et al. "Photodynamic sensitization of Leishmania amazonensis in both extracellular and intracellular stages with aluminum phthalocyanine chloride for photolysis in vitro." Antimicrobial agents and chemotherapy 49.11 (2005): 4474-4484.
Manna, Laura, et al. "Long-term follow-up of dogs with leishmaniosis treated with meglumine antimoniate plus allopurinol versus miltefosine plus allopurinol." Parasites & vectors 8.1 (2015): 289.

LeBowitz, Jonathan H. et al. "Development of a stable Leishmania expressino vector and application to the study of parasite surface antigen genes"; Proc. Natl. Acad. Sci. Vo. 87: 9736-9740; Dec. 1990.
Kurlandzka, Anna et al. The alternative pathway of haem synthesis via dehydroisocoproporphyrinogen in mutants of *Saccharaomyces cerevisiase* partially deficient in uroporphyrinogen decarboxylase activity: Biochemistry Journal; Jan. 1, 1991; 273(1):246-247.
Afonso, Susana G. et al. "Photodynamic and Non-Photodynamic Action of Several Porphyrins on the Activity of Some Heme-Enzymes" J. Enzyme Inhibition; 199; vol. 3:303-310.
LeBowitz, Jonathan H .et al. "Thymidine kinase as a negative selectable marker in Leishmanid major" Molecular and Biochemical Parasitoloty; 1992; 51:321-326.
Spikes, John D. "Photosensitizing properties of mono-L-aspartyl chlorin e6 (NPe6): a candidate sensitizer for the photodynamic therapy of tumores" J. Photochem. Photobiol. B Biol.; 1993; 14:135-143.
Kaye, Paul M. et al. "Antigens target to the Leishmania phagolysosome are processed for CDR+ T cell recognition"; Eur. J. Immunol. 1993; 23:2311-2319.
Du, Yubin et al. "Monophyletic origin of b-division proteobacterial endosymbionts and their coevoluti n with insect tryanosomatid protozoa Blastochrithidia culicis and *Crithidia* spp." Proc. Natl. Acad. Sci. Aug. 1994; 91:8437-8441.
Titus, Richard G. et al. "Development of a safe live Leishmania vaccine line by gene replacement" Proc. Natl. Acad. Sci. Oct. 1995; 92:10267-10271.
Sassa, Shigeru et al. "The role of heme in gene expression" Int. Jour. of Hematology; 1996; 63:167-178.
Castro, Dan J. "The Concept of Laser Phototherapy" Laser Apps. in Otolaryngology; Dec. 1996; 29(6):1011-1029.
Chakrabarty. R. et al. Kinetics of Entry of Virulent and Avirulent Strains of Leishmanis donovani in to Macrophages: A Possible Role of Virulence Molecules (gp63 and LPG); J. Parasitol. 1996; 82(4); 632-635.
Peng, Qian et al. "5-Aminovulinic Acid-Based Photodynamic Therapy" Cancer; Jun. 15, 1997; 79(12):2282-2308.
Abels, C. Photodynamic therapy with 5-aminolaevulnic acid-induces porphyrins of an amelanotic melanoma in vivo: J. Photochem. and Photobiol B: Biology 40; 1997; 76-83.
Wainwright, Mark; "Photodynamic antimicrobial chemotherapy (PACT)"; J. of Antimicrobial Chemotherapy; 1998; 42:13-28.
Alexander, James et al. "Leishmania mexicana Cysteine Proteinase-Deficient Mutants Have Attenuated Virulance for Mice and Potentiate a Th1 Response" J. of Immunology; 1998; 0022-7767/98; p. 6794-6801.
Gibson, S.L. et al. "Aminolaevulnic acid-induced photodynamic therapy inhibits protyporphyrin IX biosynthesis and reduces subsequent treatment efficacy in vitro"; British Jour of Cancer; 1999; 80(7):998-1004.
Chang; Kwang-Poo et al. "Leishmania Virulence and Genetic Heterogeneity" Clinics in Dermatology; 1999; 17:269-273.
Mollenkopf, Hans et al. "Intracellular Bacteria as Targets and Carriers for Vaccination" Biological chemistry 382.4 (2001): 521-532.
Sassa, Shigeru "Hematologic Aspects of the Porphyias"; Int. J. of Hematoloty; 2000; 71:1-17.
Gourley, David G. "Pt ridin reductase mechanism correlates with pterin metabolism with drug resistance in trypanosomatid parasites"; Nature Structural Biology; Jun. 2001; 8(6):521-525.
Taylor, E.L. "The advantages of aminolevulinic acid photodynamic therapy in dermatology"; J. of Dermatological Treatment; 2002 13 (Supp 1):S3-S11.
Friesen, Scott A. at al. "5-Aminolevulinic acid-based photodynamic detection and therapy of brain tumors (Review)"; Int. J of Oncology; 2002; 21:577-582.
Edgeworth, Rebecca L. et al. "Vaccine Development Against HIV-1"; Immunologic Research; 2002; 25(1):53-74.
Papadopoulou; Barbara et al. "Reduced Infectivity of a Leishmania donovani Biopterin Transporter Genetic Mutant and Its Use as an Attenuated Strain for Vaccination"; Infection and Immunity; Jan. 2002; 70(1):62-68.

(56) References Cited

OTHER PUBLICATIONS

Tetaud, Emmanuel et al. "A new expression vector for Crithidia fasciculata and Leishmania"; Molec. & Biochemical Parasitology; 2002; 120:195-204.

Bissonnette, Robert et al. "Systemic Photodynamic Therapy with Aminolevulinic Acid Induces Apoptosis in Lesional T Lymphocytes of Psoriatic Plaques" The J. of Investigative Dermatology; Jul. 2002; 119(1):77-83.

Ahmed, Sami Ben Hadj et al. "A comparative evaluation of different DNA vaccine candidates against experimental murine leishmaniasis due to L. major"; Vaccine; 2004; 22:1631-1639.

Anderson, Willard Lee et al. "Quantitation of Methionyl Peptides in Nanomole Quantities by a Fluorometric Method"; Physical Biochem.; 1978; 91:481-489.

Belkaid, Y. et al. "A method to recover, enumerate and identify lymphomyeloid cells present in an inflammatory dermal site: a study in laboratory mice"; J. of Immunological Methods; 1996; 199:5-25.

Belkaid, Y. et al. "Development of a Natural Model of Cutaneous Leishmaniasis: Power Effects of Vector Saliva and Saliva Preexposure on the Long-Term Outcome of Leishmania major Infection in the Mouse Ear Dermis"; The J. of Experimental Medicine; Nov. 16, 1998; 188(10):1941-1953.

Burchmore, Richard J.S. "Genetic characterizatoin of glucose transporter function in Leishmania mexicana"; PNAS; Apr. 1, 2003; 100(7):3901-3906.

Campbell, Kimberly et al. "DNA Immunization with the Gene Encoding P4 Nuclease of Leishmania amazonensis Protects Mice against Cutaneous Leishnaniasis"; Infection and Immunity; Nov. 2003; 71(11):6270-6278.

Campbell, Kimberly et al. "Identification and Molecular Characterization of a Gene Encoding a Protective Leishmania amazonensis Trp-Asp (WD) Protein"; Infection and Immunity, Apr. 2004; 72(4)2194-2202.

Chang, Kwang-Poo "Intracellular Multiplication of Leishmania donovani During Repeated Passages in Primary Cultures of Hamster Peritoneal Macrophages" J. Parasitology; 1978; 64(5):931-933.

Chang, Kwang-Poo et al. "Multiplication of a Human Parasite (Leishmania donovani) in Phagolysosomes of Hamster Macrophages in vitro"; Science; Aug. 20, 1976; 193:678-680.

Chang, Kwang-Poo et al. "Laboratory cultivation and maintenance of Leishmania"; Leishmaniasis; 1985; 213-244.

Chang, Kwang-Poo et al. "Leishmania model for microbial virulence: the relevance of parasite multiplicatino and pathoantigenicity" Acta Tropica; 2003; 85:375-390.

Chang, Kwang-Poo et al. "Nutritional Significance of Symbiotic Bacteria in Two Species of Hemoflagellates"; Science; Feb. 8, 1974; 183:531-532.

Chicharro, C. et al. "Lower trypanosomatids in HIV/AIDS patients"; Annals of Tropical Medicine & Parasitology; 2002; 97(1); S75-S78.

Coler, Rhea N. et al. "Immunization with a Polyprotein Vaccine Consisting of the T-Cell Antigens Thiol-Specific Antioxidant, Leishmania major Stress-Inducible Protein 1, and Leishmania Elongation Initiation Factor Protects against Leishmaniniasis"; Infection and Immunity, Aug. 2002; 70(8):4215-4225.

Cruz, Angela et al. "Double targeted gene replacement for creating null mutants"; Proc. Natl. Acad. Sci.; Aug. 1991; 88:7170-7174.

Etges, Robert et al. "Progressive disease or protective immunity to Leishmania major infection: the result of a network of stimulatory and inhibitory interactions"; J. Mol. Med.; 1998; 76:372-390.

Freedman, Daniel J. et al. "Two more independent selectable markers for stable transfection of Leishmania"; Mol. and Biochemical Parasitology; 1993; 62:37-44.

Glerum, D. Moira et al. "Clonging and Identification of HEM14, the Yeast Gene for Mitochondrial Protoporphyinogen Oxidase"; Yeast; 1996; 12:1421-1425.

Goyard, Sophie et al. "Blasticidin resistance: a new independent marker for stable transfection of Leishmania"; Mol. and Biochemical Parasitology; 2000; 108:249-252.

Chen, De-Qiao et al. "Replacement of Leishmaina N-acetylglucosamine-1-phosphate transferase gene requires episomal rescut"; Mol and Biochemical Parasitology; 1999; 100:223-227.

Chen, De-Qiao et al. "Episomal Expression of Specific Sense and Antisense mRNAs in Leishmania amazonensis: Modulation of gp63 Level in Promastigotes and Their Infection of Macrophages In Vitor" Infection and Immunity; Jan. 2000; 68(1):80-86.

Chang, K.P. et al. "Heme biosynthesis in bacterium-protozoon symbioses: Enzymic defects in host hemoflagellates and complemental role of their intracellular symbiotes"; Proc. Nat. Acad. Sci.; Aug. 1975; 72(8):2979-2983.

Chang, K.P. "Human Cutaneous Leishmania in a Mouse Macrphage Line; Propagation and Isolation of Intracellular Parasites"; Science; Sep. 12, 1980; 209:1240-1242.

Akman, Leyla et al. "Multi-Site DNA Polymorphism Analyses of Leishmania Isolates Define their Genotypes Predicting Clinical Epidemiology of Leishmaniasis in a Specific Region"; J. Eukaryot. Microbiol.; 2000; 47(6): 545-554.

Oleinick NL, Evans HH; (1998); "The photobiology of photodynamic therapy: cellular targets and mechanisms." Radiat Res 150; S146-156.

Demidova TN, Hamblin MR; (2004); "Photodynamic therapy targeted to pathogens." Int. J Immunopathol Pharmacol 17; 245-254.

Canti G., et al.; (1995); "Efficacy of photodynamic therapy against doxorubicin-resistant murine tumors." Cancer Letters 93; 255-259.

Lønning, PE; (2010); "Molecular basis for therapy resistance." Mol Oncol 4; 284-300.

Akilov OE, Kosaka S, O'Riordan K, Song X, Sherwood M, et al; (2006); "The role of photosensitizer molecular charge and structure on the efficacy of photodynamic therapy against Leishmania parasites." Chem Biol 13; 839-847.

Asilian A, Davami M; (2006); "Comparison between the efficacy of photodynamic therapy and topical paromomycin in the treatment of Old World cutaneous leishmaniasis: a placebo-controlled, randomized clinical trial." Clin Exp Dermatol 31; 634-637.

Dutta S, Ray D, Kolli BK, Chang, KP; (2005); "Photodynamic sensitization of Leishmania amazonensis in both extracellular and intracellular stages with aluminum phthalocyanine chloride for photolysis in vitro." Antimicrob Agents Chemother 49, No. 11; 4474-4484.

Enk CD, Fritsch C, Jonas F, Nasereddin A, Ingber A, et al; (2003); "Treatment of cutaneous leishmaniasis with photodynamic therapy." Arch Dermatol 139; 432-434.

Escobar P, Hernández IP, Rueda CM, Martínez F, Páez E; (2006); "Photodynamic activity of aluminium (III) and zinc (II) phthalocyanines in Leishmania promastigotes." Biomedica 26; 49-56.

Gardlo K, Horska Z, Enk CD, Rauch L, Megahed M, et al; (2003); "Treatment of cutaneous leishmaniasis by photodynamic therapy." J Am Acad Dermatol 48; 893-896.

Gardner DM, Taylor VM, Cedeño DL, Padhee S, Robledo SM, et al; (2010); "Association of acenaphthoporphyrins with liposomes for the photodynamic treatment of leishmaniasis." Photochem Photobiol 86; 645-652.

González U, Pinart M, Reveiz L, Alvar J; (2008); "Interventions for Old World cutaneous leishmaniasis."; Cochrane Database Syst Rev 8; CD005067.

World Health Organization; (2010); "Leishmaniasis: background information." Available from: http://www.who.int/leishmaniasis/en/index.html.

Ouellete M, Drummelsmith J, Leprohon P, Fadili KE, Foucher A, et al; (2008); "Drug Resistance in Leishmania." In: Myler PJ, and Fasel N, editors. Leishmania: After the Genome. Norfolf, UK: Caister Academic Press. pp. 159-176.

Alvar J, Croft S, Olliaro P; (2006); "Chemotherapy in the treatment and control of leishmaniasis." Adv Parasitol 61; 223-274.

Murray HW, Berman JD, Davies CR., Saravia NG; (2005); "Advances in leishmaniasis." Lancet 366; 1561-1577.

Llanos-Cuentas A, Calderón W, Cruz M, Ashman JA, et al; (2010); "A clinical trial to evaluate the safety and immunogenicity of the LEISH-F1+MPL-SE vaccine when used in combination with sodium stibogluconate for the treatment of mucosal leishmaniasis." Vaccine 28; 7427-7435.

(56) References Cited

OTHER PUBLICATIONS

Nascimento E, Fernandes DF, Vieira EP, Campos-Neto A, Ashman JA, et al; (2010); "A clinical trial to evaluate the safety and immunogenicity of the LEISH-F1+MPL-SE vaccine when used in combination with meglumine antimoniate for the treatment of cutaneous leishmaniasis." Vaccine 28; 6581-6587.
Brandonisio O, Spinelli R, Pepe M; (2004); "Dendritic cells in Leishmania infection." Microbes Infect 6: 1402-1409.
Chang KP, Fong D; (1983); "Cell biology of host-parasite membrane interactions in leishmaniasis." Ciba Found Symp 99; 113-137.
Soong L; (2008); "Modulation of dendritic cell function by Leishmania parasites." J Immunol 180; 4355-4360.
Kumari S, Samant M, Khare P, Misra P, Dutta S, et al; (2009); "Photodynamic vaccination of hamsters with inducible suicidal mutants of Leishmania amazonensis elicits immunity against visceral leishmaniasis." Eur J Immunol 39; 178-191.
Sah JF, Ito H, Kolli BK, Peterson DA, Sassa S, et al; (2002); "Genetic rescue of Leishmania deficiency in porphyrin biosynthesis creates mutants suitable for analysis of cellular events in uroporphyria and for photodynamic therapy." J Biol Chem 277; 14902-14909.
Dutta S, Kolli BK, Tang A, Sassa S, Chang KP; (2008); "Transgenic Leishmania model for delta-aminolevulinate-inducible monospecific uroporphyria: cytolytic phototoxicity initiated by singlet oxygen-mediated inactivation of proteins and its ablation by endosomal mobilization of cytosolic uroporphyrin." Eukaryot Cell No. 7; 1146-1157.
Porgador A, Yewdell JW, Deng Y, Bennink JR, Germain RN; (1997); "Localization, quantitation, and in situ detection of specific peptide-MHC class I complexes using a monoclonal antibody." Immunity 6; 715-726.
Shastri N, Gonzalez F; (1993); "Endogenous generation and presentation of the ovalbumin peptide/Kb complex to T cells." J Immunol 150: 2724-2736.
McKeown, NB; (1998); "Phthalocyanine Materials—Synthesis, structure and function"; Front Matter and Chapter One provided; UK: Cambridge University Press (book out of print) (27 pages).
DeRosa MC, Crutchley RJ; (2002); "Photosensitized singlet oxygen and its applications." Coord Chem Rev 233-234; 351-371.
Morris RL, Varnes ME, Kenney ME, Li YS, Azizuddin K, et al; (2002); "The peripheral benzodiazepine receptor in photodynamic therapy with the phthalocyanine photosensitizer Pc 4." Photochem Photobiol 75; 652-661.
Dutta S, Furuyama K, Sassa S, Chang KP; (2008); "*Leishmania* spp.: delta-aminolevulinate-inducible neogenesis of porphyria by genetic complementation of incomplete heme biosynthesis pathway." Exp Parasitol 118; 629-636.
Lovell JF, Liu TW, Chen J, Zheng G.; (2010); "Activatable photosensitizers for imaging and therapy." Chem Rev 110; 2839-2857.
Li H, Jensen TJ, Fronczek FR, Vicente MG; (2008); "Syntheses and properties of a series of cationic water-soluble phthalocyanines." J Med Chem 51; 502-511.
Shen Z, Reznikoff G, Dranoff G, Rock KL; (1997); "Cloned dendritic cells can present exogenous antigens on both MHC class I and class II molecules." J Immunol 158; 2723-2730.

Castro R, Scott K, Jordan T, Evans B, Craig J, et al; (2006); "The ultrastructure of the parasitophorous vacuole formed by Leishmania major"; Amer. Society of Parasitologists; J Parasitol 92; 1162-1170.
Dzierszinski F, Pepper M, Stumhofer JS, LaRosa DF, Wilson EH, et al; (2007); "Presentation of Toxoplasma gondii antigens via the endogenous major histocompatibility complex class I pathway in nonprofessional and professional antigen-presenting cells." Infect Immun 75; 5200-5209.
Liu X, Chang KP; (1994); "Identification by extrachromosomal amplification and overexpression of a zeta-crystallin/NADPH-oxidoreductase homologue constitutively expressed in *Leishmania* spp." Mol Biochem Parasitol 66; 201-210.
Mills IG, Jones AT, Clague MJ; (1999); "Regulation of endosome fusion." Mol Membr Biol 16; 73-79.
Varela MRE, Muñoz DL, Robledo SM, Kolli BK, et al; (2009); "Leishmania (Viannia) panamensis: an in vitro assay using the expression of GFP for screening of antileishmanial drug." Exp Parasitol 122; 134-139.
Lyons AF, Parish CR.; "Determination of lymphocyte division by flow cytometry." J Immunol Methods.; 1994; 171(1):131-7.
Shen, Z., G. Reznikoff, G. Dranoff, and K.L. Rock; 1997; "Cloned dendritic cells can present exogenous antigens on both MHC class 1 and class II molecules." J Immunol. 158:2723-2730.
Vidard L, Rock KL, Benacerraf B.; "Diversity in MHC class II ovalbumin T cell epitopes generated by distinct proteases." J Immunol. 1992; 149:498-504.
Mallet-Designe VI, Stratmann T, Homann D, Carbone F, Oldstone MB, Teyton L.; "Detection of low-avidity CD4+ T cells using recombinant artificial APC: following the antiovalbumin immune response." J Immunol.; 2003 170(1):123-31.
Dutta S, Chang C, Koli BK, Sassa S, Yousef M, Showe M, Showe L, Chang KP; "Delta-aminolevulinate-induced host-parasite porphyric disparity of selective photolysis of transgenic Leishmania in the phagolysosomes of mononuclear phagocytes: a potential novel platform for vaccine delivery.": Eukaryot Cell Apr. 2012, 11(4):430-41.
Adler, S.; "the Behaviour of a Lizard Leishmania in Hamsters and Baby Mice" Rev. Inst. Med.; 1962; 4(2): 61-64.
Oloso, J.O. et al.; "Uptake of promastigotes of a lizard *Leishmania* sp. and Leishmania donorani by mouse perioneal macrophages"; Acta Tropica; 1983; 40: 89-91.
Roszental, S. et al. "Influence of the endosymbiont on the interaction of Crithidia deanei with macrophages"; Microse Electron Biol. Cell; 1987; 11:167-179.
Hughes, Austin L. et al.; "Phylogeny of Trypanosomatidae and Bodonidae (Kinetoplastida) Based on 18S rRNA: Evidence for Paraphyly of Trypanosoma and Six Other Genera"; Mol. Biol. Evol.; 2003; 20(4):644-652.
Vaccaro; D.E.; "Symbiosis therapy: the potential of using human protozoa for molecular therapy"; Mol. Ther. 2(6)535-538, Dec. 2000.
Breitling, Reinhard et al. "Non-pathogenic trypanosomatid protozoa as a platform for protein research and production" Protein Expression and purification 25 (2002) 209-218.
Wang, Wei-yeh et al. "Genetic control of Chlorophyll Biosynthesis in Chlamydomonas: Analysis of a Mutant Affecting Syntesis of -Aminolevulinic Acid" Cell 6: 75-84, Sep. 1975.

\* cited by examiner

IMMUNOTHERAPY OF CANINE LEISHMANIASIS

RELATED APPLICATIONS

The present invention claims the benefit of U.S. Provisional Patent Application No. 62/502,214 filed May 5, 2017, the contents of which are incorporated herein by reference.

FIELD OF THE INVENTION

The present invention provides an immunotherapy of canine leishmaniasis by photodynamic vaccination.

BACKGROUND OF THE INVENTION

Photodynamic therapy (PT) eliminates diseased cells/pathogens by using photosensitizers (PS) that are excitable by light to produce cytotoxic reactive oxygen species (ROS) in the presence of oxygen. Since the ROS simultaneously attack multiple molecules of very different properties, PT is considered to have the potential to circumvent the problem of drug-resistance common to both infectious and non-infectious diseases. By their innate ability to dwell in the endosome/phagolysosomes of antigen-presenting cells, *Leishmania* are a suitable carrier for vaccine delivery.

A novel cell-mediated immunotherapy is being developed according to the *Leishmania* strategy of vaccine delivery (Chang et al., 2016 Parasit Vectors. 9:396) against difficult-to-cure diseases, e. g., canine leishmaniasis. The current clinical management of this disease entails prolonged treatments of sick dogs for 30 days with heavy daily dosage of very toxic drugs (antimonials/miltefosine) followed by a daily maintenance dose of allopurinol for life. Still, relapses of the disease are frequent (up to 50%) within the first year (Manna et al., 2015 Parasit Vectors. 8: 289).

Commonly assigned U.S. Pat. Nos. 7,261,887; 7,238,347; 9,327,017, and U.S. Patent Publication No. 2017/0042989 disclose using *leishmania* as a carrier for vaccine delivery or for the delivery of peptides and proteins. All of these documents are incorporated herein by reference.

SUMMARY OF THE INVENTION

The present invention provides a method of treating leishmaniasis in canines using a combination of chemotherapy and immunotherapy by photodynamic vaccination. The method includes the steps of administering an effective amount of a chemotherapeutic agent to a canine diagnosed with leishmaniasis and a solution containing a photo-inactivated *Leishmania* at $10^7/0.1$ ml.

DETAILED DESCRIPTION OF THE INVENTION

While this invention is susceptible of embodiments in many different forms, and will be described herein in detail, specific embodiments thereof with the understanding that the present disclosure is to be considered as an exemplification of the principles of the invention and is not intended to limit the invention to the specific embodiments illustrated.

Method of Treating Canine Leishmaniasis

With institutional IRB-approval and dog owner's consent, a direct observational open label trial was initiated for immunotherapy of 20 diseased dogs, of which 9 were each immunized with frozen photoinactivated *Leishmania* at $10^7/0.1$ ml and 11 similarly immunized after s.c. chemotherapy with meglumine antimoniate at 100 mg/kg/day for 30 days followed by allopurinol at a maintenance dose of 10 mg/kg/day. All dogs were assessed clinically for disease signs, blood-biochemical profiles, anti-*Leishmania* antibodies by IFAT, and parasite loads of lymphnode aspirates by quantitative real-time RT-PCR of *Leishmania* DNA every 3 months for >3 years.

Results. Prognosis was improved for the group with immunotherapy after the initial 30 day-chemotherapy based on clinical scores and parasite loads assessed. The immunotherapy was found to stop relapse of the disease completely when used together with allopurinol and worked better than using allopurinol alone.

Suitable chemotherapeutic agents include antimony-containing compounds, for example, meglumine antimoniate or glucantime®, sodium stibogluconate or Pentostam®.

In one form of the invention the *Leishmania* is exposed to a photosensitizer. The photosensitizer is taken up by endocytosis or via plasma membrane penetration. The photosensitizer resides in an organelle or cytosol of the *Leishmania*.

Suitable photosensitizers include those set forth in U.S. Patent Publication No. 2017/0042989 and U.S. Pat. No. 9,327,017. In one form of the invention the photosensitizer is selected from phthalocyanines, naphthalocyanines, porphyrins, chlorins and bacteriochlorins.

Conclusions/Significance: When applied appropriately, the immunotherapy appears to boost the feeble immunity expected to develop after chemotherapy. Work is on-going to see if it is robust enough to clear the infection completely from immunized dogs, and to enroll additional dogs for both prophylactic and therapeutic trials.

The appended claims should be construed broadly and in a manner consistent with the spirit and the scope of the invention herein.

We claim:

1. A method of treating canine leishmaniasis comprising:
administering a chemotherapeutic agent to a canine diagnosed with canine leishmaniasis, an antimony containing compound meglumine antimoniate s.c. at 100 mg/kg/day for a 30 day period followed by s.c. allopurinol at a daily maintenance dose of 10 mg/kg/day; and
periodically administering immunotherapy to the canine with a vaccine solution containing a photo-inactivated *Leishmania* at $10^7/0.1$ ml after the chemotherapeutic agent meglumine antimoniate administration is completed.

2. The method of claim 1 wherein the Leishmania contains a photosensitizer selected from the group consisting of phthalocyanines, naphthalocyanines, porphyrins, chlorins and bacteriochlorins.

3. The method of claim 2 wherein the photosensitizer is a phthalocyanine or a porphyrin derivative.

4. The method of claim 3 wherein the photosensitizer is cationic and soluble.

5. The method of claim 3 wherein the phthalocyanine is selected from those with amino groups, anilinium types and pyridyloxy types.

6. The method of claim 2 wherein the photosensitizer resides in an organelle of the Leishmania or its cytosol.

7. The method of claim 2 wherein the photosensitizer is taken up into the *Leishmania* by endocytosis or via plasma membrane penetration.

8. The method of claim 1 wherein the step of periodically administering a solution to the canine containing a photo-inactivated Leishmania occurs 1-3 times during a second 30 day period.

* * * * *